(12) United States Patent
Scott

(10) Patent No.: US 6,362,351 B2
(45) Date of Patent: Mar. 26, 2002

(54) CATALYST AND METHOD FOR AMIDE FORMATION

(75) Inventor: William Leonard Scott, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/790,336

(22) Filed: Feb. 22, 2001

Related U.S. Application Data

(62) Division of application No. 09/633,936, filed on Aug. 8, 2000, which is a division of application No. 09/213,734, filed on Dec. 17, 1998, now Pat. No. 6,121,471.
(60) Provisional application No. 60/068,400, filed on Dec. 22, 1997.

(51) Int. Cl.[7] ............................................. C07C 231/00

(52) U.S. Cl. ........................................... 554/59; 554/58

(58) Field of Search ...................... 554/69, 68

(56) References Cited

U.S. PATENT DOCUMENTS 3,725,380 A    4/1973   Konig et al. ............. 260/112.5

OTHER PUBLICATIONS

Pop. et al.,J. Org. Chem., vol. 62, No. 8, pp. 1–15.*
Pop,I.E., et al. Versatile Acylation of N–Nucleophiles Using a New Polymer–Supported 1–Hydroxybenzotriazole Derivative. J. Org. Chem. 1997, vol. 62, No. 8, pp. 1–15.

* cited by examiner

Primary Examiner—Deborah D. Carr
(74) Attorney, Agent, or Firm—Charles T. Joyner

(57) ABSTRACT

The invention is a catalyst, the use of the catalyst and a method of using the catalyst in the formation of a compound with an amide bond. The catalyst is an HOBT derivative having the following formula (1):

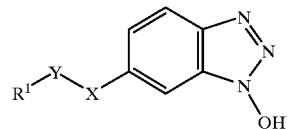

where $R^1$ is a group bearing a positive charge at pH 5–7; where Y is a bond or a substituted or unsubstituted alkylene chain containing 1–10 carbon atoms and 0–2 heteroatoms selected from the group consisting of N, S and O; and where X is a linker group selected from —CO— or —SO$_2$—. In the method, an amine, a carboxylic acid, an amide coupling agent and a catalyst of formula (1) are reacted for a time sufficient to produce an amide bond between the amine and the carboxylic acid. Thereafter, the compound containing the amide bond is isolated.

1 Claim, No Drawings

CATALYST AND METHOD FOR AMIDE FORMATION

CROSS-REFERENCE TO RELATED APPLICATIONS

This application is a divisional application of pending divisional U.S. Ser. No. 09/633,936, filed Aug. 8, 2000, which is a division of Ser. No. 09/213,734, filed Dec. 17, 1998, now U.S. Pat. No. 6,121,471 which claims the benefit of Ser. No. 60/068,400, filed Dec. 22, 1997, the contents of which are herein incorporated by reference.

BACKGROUND OF THE INVENTION

This invention provides a novel catalyst and method for the formation of amide bonds. The catalysts are derivatives of hydroxybenzotriazole (HOBT) and carry a positive charge at pH 5–7. These reagents are useful for forming compounds containing an amide bond with high purity and yield.

A wealth of procedures are available for forming amide bonds. Nonetheless, there is still room for improvement. For example, procedures have been developed which use reagents such as carbodiimides as amide coupling agents. These carbodiimides include dicyclohexylcarbodiimide (DCC), diisopropylcarbodiimide (DIC), and 1-(3-dimethylaminopropyl)-3-ethylcarbodiimide hydrochloride (EDC). Unfortunately, these particular reagents can require a large excess of acid, can be problematic for difficult couplings with unreactive carboxylic acids and/or amines and can be difficult to purify from the reaction mixture.

Catalysts such as 1-hydroxybenzotriazole (HOBT) and derivatives thereof have also been used.

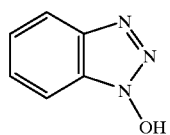

HOBT

Unfortunately, HOBT and its derivatives can be difficult to remove from the reaction media.

SUMMARY OF THE INVENTION

Briefly stated, the invention is a catalyst, the use of the catalyst and a method of using the catalyst in the formation of a compound with an amide bond. The catalyst is an HOBT derivative having the following formula (1):

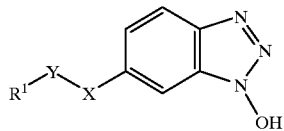

where $R^1$ is a group bearing a positive charge at pH 5–7; where Y is a bond or a substituted or unsubstituted alkylene chain containing 1–10 carbon atoms and 0–2 heteroatoms selected from the group consisting of N, S and O; and where X is a linker group selected from —CO— or —SO$_2$—.

In accordance with the method aspect of the invention, an amine, a carboxylic acid, an amide coupling agent and a catalyst of formula (1) are reacted for a time sufficient to produce an amide bond between the amine and the carboxylic acid. Thereafter, the compound containing the amide bond is isolated.

In accordance with a preferred method, the reaction is carried out in solution. Also, the amide coupling agent is a carbodiimide, which carbodiimide bears a positive charge at pH 5–7. The catalyst is most preferably PP-HOBT (see formula (2) below). Finally, the compound containing the amide bond preferably does not bear a positive charge at pH 5–7 and is isolated by passing the entire reaction mixture through a cation exchange resin which traps unwanted materials and allows the desired amide product to be isolated from the eluent with excellent purity.

This preferred method, wherein the amide coupling agent and catalyst both carry a positive charge at pH 5–7, provides the advantage that the compound containing the amide bond can be readily isolated from the reaction mixture when the mixture is passed through a cation exchange resin.

As used herein and the appended claims, the term "catalyst" is intended to have a relatively broad meaning referring to a compound that facilitates the reaction between one or more other compounds, the catalyst remaining in or returning to its original state.

As used herein and the appended claims, "alkyl" means an unbranched or branched aliphatic or cyclic group containing 1–20, preferably 1–10, carbon atoms.

As used herein and the appended claims, "alkylene" means an unbranched or branched carbon chain containing 1–20, preferably 1–10, carbon atoms. Branched carbon chains include both linear and cyclic structures.

As used herein and the appended claims, "aryl" means a mono- or polycyclic carbocyclic aromatic ring containing 6 to 10 carbon atoms, such as phenyl (Ph) or naphthyl. When more than 1 ring is present, the rings can be fused or unfused.

As used herein and the appended claims, "heteroaryl" is a mono-, bi- or tricyclic, N-, O- or S-heteroaryl, such as benzofuran, benzothiophene, furan, imidazole, indole, isothiazole, oxazole, piperazine, pyrazine, pyrazole, pyridazine, pyridine, pyrimidine, pyrrole, quinoline, thiazole, and thiophene.

DETAILED DESCRIPTION OF PREFERRED EMBODIMENTS

The catalysts of the present invention have the general formula (1):

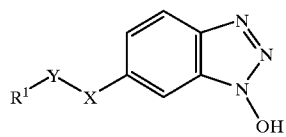

where $R^1$ is a group bearing a positive charge at pH 5–7;
Y is a bond or a substituted or unsubstituted alkylene chain containing 1–10 carbon atoms, and, optionally 1 or more heteroatoms such as N, S or O; and
X is a linker group selected from —CO— or —SO$_2$—.

The function of $R^1$ is to allow the catalyst of the present invention to be removed by a cation exchange resin; thereby allowing the formed compound containing the amide bond to be purified via ion exchange chromatography. $R^1$ can be any group bearing a positive charge at pH 5–7. $R^1$ is preferably a substituted or unsubstituted, aliphatic or cyclic, dialkylamine (such that $R^1$ is a tertiary amine in formula (1)). Preferably, $R^1$ is a cyclic dialkylamine such as piperidine. Most preferably, Y is a bond and $R^1$ is 4-piperidino-piperidine.

Y is preferably a substituted or unsubstituted alkylene chain containing 1–10 carbon atoms.

The substituents for $R^1$ and Y can be selected for optimization of the solubility characteristics of the catalyst in various solvents. For example, as the number of carbon atoms in the Y substituent increases, the solubility of the catalyst in nonpolar solvents is expected to improve. Alternatively, groups such as ethers and the like can be added to the $R^1$ or Y to enhance solubility in polar solvents.

Suitable substituents for $R^1$ and Y include groups which are relatively unreactive with carboxylate groups and amine groups. Examples include $C_{1-6}$ alkyl, $C_{1-6}$ alkoxy, and halogen. Amines and carboxylates are not typically suitable substituents as this would cause the catalyst to react with the starting materials, resulting in undesired side products. Presently, —$SO_2$— is preferred as the linker group X.

The most preferred embodiment of the present invention is a catalyst of the formula (2):

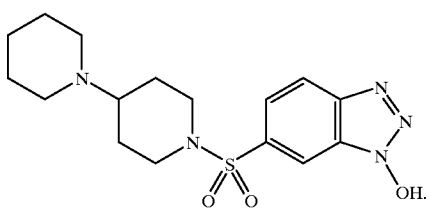

This particular catalyst has acceptable solubility in DMF and can be readily removed from the reaction mixture by passing the mixture through a cation exchange resin.

Preparation of the Catalyst

This most preferred catalyst, which includes a sulphonamide linker group X, may be synthesized in accordance with the following:

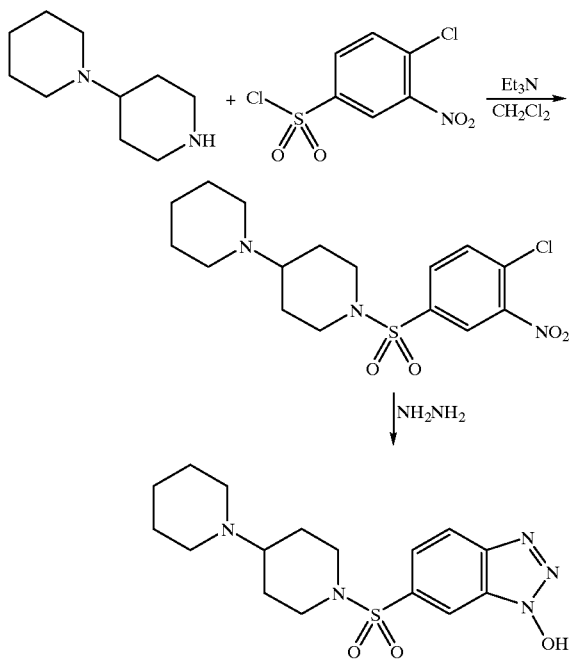

The chemistry depicted in this scheme is derived from Pop et al. (J. Org. Chem. 1997, 62:2594, the disclosure of which is incorporated herein by reference), who described the preparation of a resin bound HOBT.

When X is a carbonyl group, the catalysts may be prepared from 6-acyl chloride-HOBT as shown below:

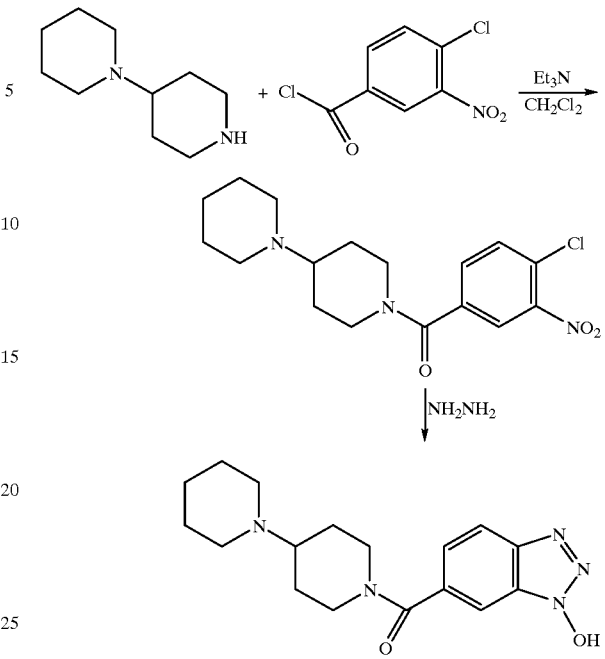

Method of Amide Bond Formation

The invention provides a method of forming a compound containing an amide bond. The steps comprise reacting an amine, a carboxylic acid, a coupling agent and a compound of the general formula (1) described above. The general reaction is represented by the following:

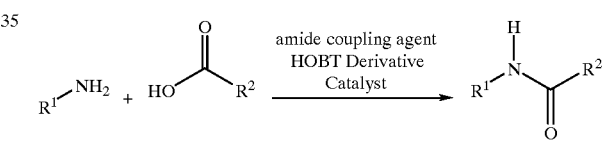

The reaction is carried out under conditions and for a time sufficient to produce an amide bond between the amine and the carboxylic acid.

Suitable amines ($R^1$) include any compounds containing a free primary or secondary amine, including, for example, substituted or unsubstituted alkylamines, dialkylamines, arylamines and heteroarylamines. As is commonly done, HCl salts or other salts of the amines can also be used as the starting materials.

Use of the catalyst of the invention provides an advantage when the amine used in the amide formation reaction is provided in the form of an HCl salt. Typically, when using an HCl salt of an amine, a separate base is added to the reaction mixture to liberate the amine. However, the present catalyst, particularly with the tertiary amine in the $R^1$ group, can fill this role and eliminate the necessity to add a separate base to the reaction mixture.

Suitable carboxylic acids ($R^2$—$CO_2H$) include any compounds containing a free carboxylate, including, for example, substituted or unsubstituted alkylcarboxylates, arylcarboxylates or heteroarylcarboxylates.

The above amines and carboxylates can be substituted 1 or more times (preferably 1 to 3 times) with a halogen, hydroxyl, amine, alkylamine, dialkylamine, alkyl, alkoxy, alkenyl, alkylcarboxylate, thiol, and alkylcarboxyamide. In addition, the starting amines and carboxylic acids may have protected functional groups.

In one aspect of this invention, the catalyst of the present invention is used in the formation of peptide bonds between a first amino acid containing moiety and a second amino acid containing moiety. Each of these amino acid containing moieties can include one or more amino acids. Suitable amino acids include naturally encoded amino acid residues, unusual or unnatural amino acid residues, and synthetic amino acid residues.

Preferably, the compound containing an amide bond produced by the method of the present invention is one that does not bear a positive charge at pH 5–7. In this way, the compound can be isolated from the catalyst by passing the reaction mixture through a cation exchange resin.

Typically, amide coupling agents are compounds that function as dehydrating agents, thus driving the condensation reaction between a carboxylic add and an amine. Preferably, the amide coupling agent is a compound that bears a positive charge at pH 5–7. In this way, the amide coupling agent may be removed from the reaction solution by the same cation exchange resin as that used for the catalyst. Alternatively, the coupling agent does not bear a positive charge and other means are used to remove it from the reaction mixture. For example, precipitation of the byproduct of the coupling agent. Moreover, other conventional chromatographic means may be used to remove the amide coupling agent.

Suitable amide coupling agents include benzotriazolyloxy-tris(dimethylamino) phosphonium Hexafluorophosphate (BOP) and carbodiimides such as dicyclohexylcarbodiimide (DCC), diisopropylcarbodiimide (DIC), and 1-(3-dimethylaminopropyl)-3ethylcarbodiimide hydrochloride (EDC). EDC is the most preferred carbodiimide to use as the amide coupling agent.

Preferably, the reaction is carried out in solution. This is particularly advantageous because the catalyst, and preferably the amide coupling agent as well, can be removed from the reaction solution by passing the solution through a cation exchange resin. Alternatively, the reaction is carried out on solid phase, for example, a solid phase peptide synthesis such as that described in U.S. Pat. No. 4,888,385, the disclosure of which is incorporated herein by reference.

Suitable solvents for the reaction include non-nucleophilic organic solvents, such as dimethylformamide (DMF), dimethylsulfoxide (DMSO), methylene chloride (DCM or $CH_2Cl_2$) and the like.

The reaction is typically conducted for at least 30 minutes to 24 hours. Preferably, the reaction is conducted for about 12 hours.

The reaction is typically conducted at room temperature (about 25° C.), although any reaction temperature conducive to the reaction can be used.

The compound containing the amide bond can be isolated using conventional purification means, including, for example, extraction, chromatography, crystallization, etc. However, the preferred method of isolation involves passing the reaction mixture through a cation exchange resin. Preferred cation exchange resins include silica based resin substituted with functional groups, including SCX (benzensulfonic acid resin), PRS (propylsulfonic acid resin) and CBA (carboxylic acid resin); all of which are available from Varian Sample Preparation (Harbor City, Calif.). The compound containing the amide bond will wash through the column, while the catalyst, and preferably the amide coupling agent as well, will bind to the column. Preferably, about 1 g of resin is used per 0.7 to 1 eq of catalyst.

Using this latter technique the compound containing the amide bond can be isolated with greater than 95% purity.

The method of the preferred embodiment typically results in greater than about 60% yield of compound containing an amide bond. As noted below, it has been observed that, in comparing otherwise identical amide formation reactions, the presence of the PP-HOBT catalyst made a significant improvement in the yield over that without its presence.

EXAMPLES

The following examples are provided as illustration only, and are not intended to limit this invention in any way.

Example 1

Procedure for Preparation of PP-HOBT

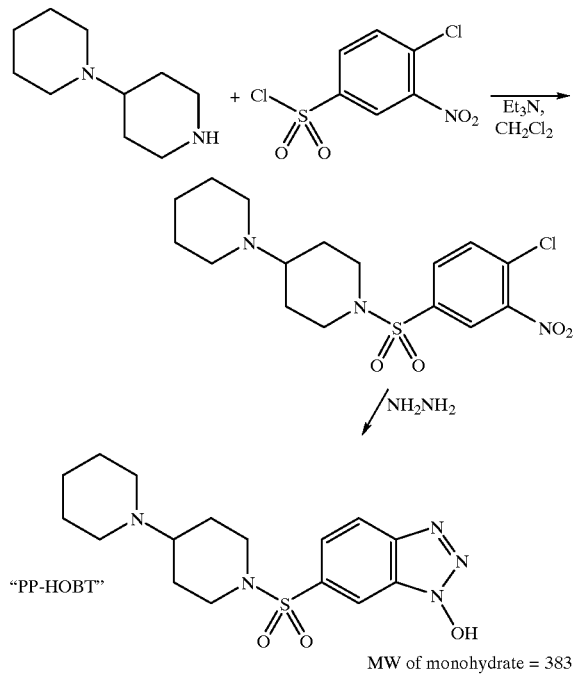

"PP-HOBT"

MW of monohydrate = 383

Starting Materials:
   4-chloro-3-nitrobenzenesulfonyl chloride (MW=256) (available from Aldrich) Triethylamine (MW=101)
   4-piperidino-piperidine (MW=168) (available from Aldrich, 90%, Lot #11033PG) Hydrazine hydrate Procedure:
   To a stirred solution of 7.68 g (30 mmol) sulfonyl chloride in 120 ml of dichloromethane was added dropwise, over a 10 min period, 5.049 (30 mmol) of 4-piperidino-piperidine and 3.6 g (36 mmol) of triethylamine in 30 ml of dichloromethane. A mildly exothermic reaction ensued. After stirring 2 hours at room temperature the orange solution was diluted with 100 ml of dichloromethane and washed with 2, 100-ml portions of 10% sodium bicarbonate solution and 100 ml of brine. After drying (sodium sulfate) solvent was removed at reduced pressure to afford 10.7 g of crude product as a light tan solid ($R_f$=0.5, Silica, 10% MeOH/chloroform).

To this crude material was added 200 ml of 95% EtOH/5% MeOH followed by 60 ml of hydrazine hydrate. The mixture-was refluxed for 3 hours. Over the first ½ hour the initially orange solution turned deep red-orange before turning orange again. At the end of the three hour reflux period most of the solvent, water and hydrazine was removed at reduced pressure. To the residue was added 50 ml of EtOH and solvent removed at reduced pressure. This was repeated 2 or more times to give a tan solid which was further dried in the vacuum oven to a constant weight of 13.5 g.

To the flask containing this solid was added 250 ml of water. Almost all of the solid went into solution, then a fine light yellow precipitate formed. After stirring, the mixture was cooled in an ice bath for two hours. The solid was collected by vacuum filtration through a sintered glass filter, and rinsed with about 20 ml of cold water. Drying in the vacuum oven at 40° overnight afforded 7.3 g of product as an off-white crunchy powder, mp 195–200 (dec). The elemental analysis was consistent with the compound existing as a monohydrate. With a production of 7.3 g (19 mmol) the yield was calculated as 63%.

An analog of PP-HOBT was prepared using the same procedure but substituting 3-dimethylamino propylamine for the 4-piperidino-piperidine. This material was poorly soluble in DMF and dichloromethane.

Example 2

Procedure for Amide Formation Using SCX to Remove Excess Amine, EDC, Urea and the PP-HOBT Catalyst

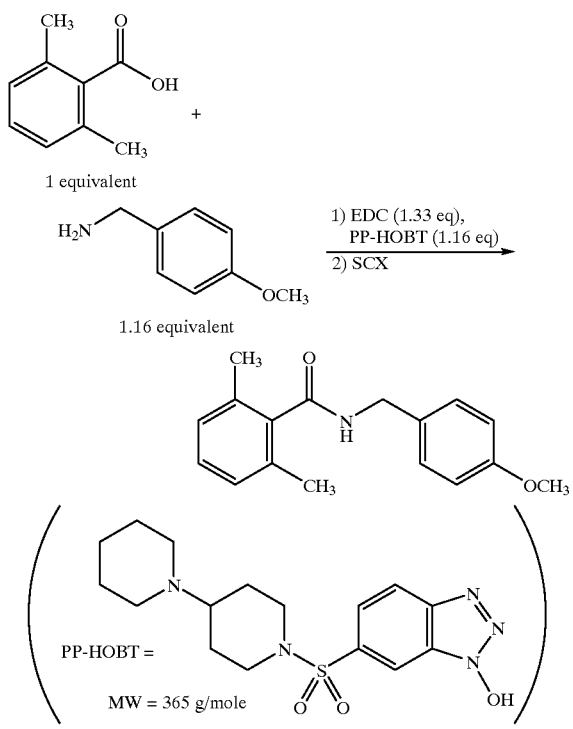

Starting Materials:
  2,6-dimethyl benzoic acid (MW=150)
  4-methoxy benzyl amine (MW=137)
  EDC HCl salt (MW=191.7)
  PP-HOBT (MW=365)
  DMF, CH$_2$Cl$_2$
Procedure:
  The following stock solutions were prepared:
  0.1 M acid in 10% DMF/DCM
  0.35 M amine in 10% DMF/DCM
  0.175 M PP-HOBT in DMF (heat to get into solution)
  0.1 M EDC HCl salt in DCM In a 3 ml vial was added 0.3 ml (30 umol, 1 eq) of the acid stock solution followed by 0.1 ml (35 umol, 1.16 eq) amine stock solution, 0.2 ml (35 umol, 1.16 eq) PP-HOBT stock solution and, finally, 0.4 ml (40 umol, 1.33 eq) EDC solution. The capped vial was gently rotated for 12 hours, uncapped, and the heterogeneous reaction mixture diluted with 0.5 ml of MeOH. This mixture was applied to a 500 mg SCX column pre-washed with 2.5 ml of MeOH and 2.5 ml of 10% MeOH/CHCl$_3$. After pushing through the solution with nitrogen, the column was washed with 2.5 ml of 10% MeOH/CHCl$_3$. Evaporation of solvent, first under nitrogen on the hot plate and then in the vacuum oven, afforded 7.5 mg (28 umol, 93% yield) of product which was pure by NMR.

Examples 3 and 4

Comparison of Amide Formation with and without PP-HOBT

To verify the ability of PP-HOBT to catalyze amide formation the following experiments were performed:

Example 3

Amide Formation With PP-HOBT

In a 3 ml vial was added 0.3 ml (30 umol, 1 eq) of the acid stock solution followed by 0.1 ml (35 umol, 1.16 eq) amine stock solution, 0.2 ml (35 umol, 1.16 eq) PP-HOBT stock solution and, finally, 0.4 ml (40 umol, 1.33 eq) EDC solution. The capped vial was gently rotated for 2 hours, uncapped, and the heterogeneous reaction mixture diluted with 0.5 ml of MeOH. This mixture was applied to a 500 mg SCX column pre-washed with 2.5 ml of MeOH and 2.5 ml of 10% MeOH/CHCl$_3$. After pushing through the solution with nitrogen, the column was washed with 2.5 ml of 10% MeOH/CHCl$_3$. Evaporation of solvent, first under nitrogen on the hot plate and then in the vacuum oven, afforded 7.5 mg of crude product which contained 70% desired amide product and 30% starting acid by NMR.

Example 4

Amide Formation Without PP-HOBT

Example 4 was done under identical conditions to 3 except that no PP-HOBT was added to the reaction mixture. Evaporation of solvent, first under nitrogen on the hot plate and then in the vacuum oven, afforded 4.0 mg of crude product which contained <5% desired amide product and 95% starting acid by NMR.

Having now fully described the invention, it will be apparent to one of ordinary skill in the art that many changes and modifications can be made thereto without departing from the spirit or scope of the invention as set forth herein.

What is claimed is:

1. A method of forming and isolating a compound containing an amide bond, comprising the steps of:

forming a reaction mixture comprising an amine, a carboxylic acid, a carbodimide agent and a compound of the formula (2):

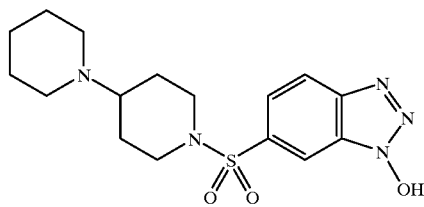
reacting said reaction mixture under conditions and for a time sufficient to produce an amide bond between the amine and the carboxylic acid; and
isolating the compound containing the amide bond by passing the entire reaction mixture through a cation exchange resin.
* * * * *